United States Patent [19]

Herschler

[11] 4,177,267

[45] Dec. 4, 1979

[54] ENHANCING TISSUE PENETRATION OF PHYSIOLOGICALLY ACTIVE STEROIDAL AGENTS WITH DMSC

[75] Inventor: Robert J. Herschler, Camas, Wash.

[73] Assignee: Crown Zellerbach, San Francisco, Calif.

[21] Appl. No.: 304,283

[22] Filed: Nov. 6, 1972

Related U.S. Application Data

[60] Division of Ser. No. 69,155, Sep. 2, 1970, Pat. No. 3,711,606, which is a continuation-in-part of Ser. No. 753,231, Aug. 16, 1968, Pat. No. 3,551,554, which is a continuation-in-part of Ser. No. 329,151, Dec. 9, 1963, abandoned.

[51] Int. Cl.$^2$ .................... A61K 31/10; A61K 37/40
[52] U.S. Cl. .................................. 424/238; 424/240; 424/241; 424/242; 424/243; 424/337
[58] Field of Search .................. 424/238, 243, 337

[56] References Cited

U.S. PATENT DOCUMENTS 2,942,008  6/1960  Lubowe ............................... 252/364

OTHER PUBLICATIONS

Faust, American Perfumer 77(1); 23–26, Jan. 1962, "Some New Components for Cosmetic and Dermatologic Vehicles".
Marson, Boll. Chimicofarm 102:109–124, Feb. 1963, "Dimethylsulfoxide, A Water–Mimotic Solvent".
Brown et al., J. Pharm. Pharmacol. 15:688–692, Oct. 1963, A Note on the Toxicity and Solvent Properties of Dimethyl Sulphoxide.
Stoughton et al., "Archives of Dermatology," vol. 90, pp. 512–517, Nov. 1964.
Stoughton, "Archives of Dermatology," vol. 91, No. 6, pp. 657–660, Jun. 1965.
Kligman, "Journal of the American Medical Association", 193(10), pp. 796–804; (11), pp. 923–928, Sep. 1965.

*Primary Examiner*—Shep K. Rose
*Attorney, Agent, or Firm*—Corwin R. Horton; Stanley M. Teigland

[57] ABSTRACT

A method of enhancing tissue penetration of physiologically active steroidal agents by conjointly applying them to the tissue with dimethyl sulfoxide. Penetration of the skin and the mucous membranes of the body cavities by these agents may be enhanced by conjoint application of such agents and dimethyl sulfoxide directly to such membranes. Preferably, for penetration of these agents through the skin compositions of DMSO at concentrations of 50% and above are employed and for penetration through mucous membranes, compositions including DMSO at concentrations of 10% and above are employed. Steroidal agents may be advantageously administered by injection with DMSO in concentrations preferably up to 20% by weight to enhance penetration of internal tissue membrane barriers to achieve better distribution of these agents.

10 Claims, No Drawings

ENHANCING TISSUE PENETRATION OF PHYSIOLOGICALLY ACTIVE STEROIDAL AGENTS WITH DMSC

CROSS REFERENCES TO RELATED APPLICATION

This is a division of application Ser. No. 69,155, filed Sept. 2, 1970 now U.S. Pat. No. 3,711,606, which in turn is a continuation in part of co-pending application Ser. No. 753,231, filed Aug. 16, 1968, now U.S. Pat. No. 3,551,554 which is, in turn, a continuation in part of application Ser. No. 329,151, filed Dec. 9, 1963, now abandoned.

BACKGROUND OF THE INVENTION

A predominant and limiting problem in the development and use of physiologically active agents is the inability to administer them as effectively as is desired. In particular, there is often a limitation as to the routes of administration because of the following factors:

(1) Some agents are inactivated in the gastrointestinal tract or they are absorbed poorly into the body from the tract. Also, undesirable side effects may result which prevent effective oral administration.

(2) In every case where injection must be resorted to, there is a risk of needle injury, infection and other trauma (including the emotional trauma inevitably associated with injections).

(3) Few agents are absorbed through the skin or mucous membranes in effective quantities and the rate of absorption is less than would be desirable for those that do.

(4) A local concentration for a local effect is often desired but a larger systemic dose must be given to achieve an effective concentration at the local area when the agent can only be injected or given orally (but not topically). This higher dose often causes undesirable side effects, since dosage-related side effects are very prevalent for many agents.

Animal tissues comprise various membranes which are selectively permeable and which allow some substances to pass freely, while rejecting others or permitting only slight passage. Such membranes comprise the body coverings and externally communicating cavities, including the skin and mucous membranes of the body cavities, e.g. alimentary tract, respiratory tract, genitourinary tract, oral cavity, eyes, etc. (collectively defined herein as external membranes). They also include internal membranes such as the linings of the various organs and other internal body structures, e.g. peritoneum and pleura, and the membranes surrounding cellular and intracellular structures. It is desirable in overcoming the aforementioned problems in drug administration to increase the passage or penetration of agents across such membranes and further to enhance their intercellular and intracellular diffusion in order for them to reach their situs of activity more rapidly to achieve the desired response more quickly and often more effectively. It is exceptionally desirable to do this in a reversible manner, by which is meant penetration of the agents into tissue without adversely affecting or impairing the function or structure of the tissue. It is known that certain substances will penetrate tissue only after the tissue has been irreversibly damaged, which is certainly undesirable. Certain agents, such as surfactants, have been known previously for increasing penetration of various agents. However, again such penetration was effected only through irreversible damage of the tissue.

It has been a major rule in medicine that the "vehicles" or "carriers" have relatively little effect on the penetration rate for a given agent and this rule generally still holds true. Thus, with conventional carriers for medicines, such as alcohol, carbowax, water, etc., few agents will adequately penetrate such formidable external membrane barriers as the intact skin or mucous membrane. It is to be expected that this would be true of all potential "vehicles" or materials combined with physiologically active agents. However, surprisingly, it has been discovered that dimethyl sulfoxide (DMSO) has the unusual ability to greatly enhance the penetration of agents when they are applied to such membrane barriers along with dimethyl sulfoxide. The penetration of agents which previously have not penetrated these membranes to an effective degree may be enhanced sufficiently so that a useful result may be obtained. The penetration of agents which have been known to penetrate to a limited degree in conventional vehicles may be significantly enhanced. New and convenient routes of administration, often with a decrease in side effects of the agents, better localized concentration and a more sustained activity, may thereby be created for many agents.

In my co-pending application Ser. No. 615,377, filed Feb. 13, 1967, is disclosed my related discovery that DMSO enhances the penetration of plant-active agents (pesticides, dyes, nutrients, hormones, herbicides and the like) into plant tissue in a highly unusual manner.

Dimethyl sulfoxide is a water-white liquid at room temperature having a freezing point of approximately 18.5° C. and a specific gravity of approximately 1.1. Dimethyl sulfoxide is a well known industrial solvent and it has been available in commercial quantities for at least a decade (from Crown Zellerbach Corporation, San Francisco, Calif.). DMSO was originally synthesized in 1866 and since that time it has been extensively investigated for possible industrial and biological utility and a considerable amount of literature has developed on its properties and uses. Over the last 25 years it has found widespread use as a solvent in industry and in the laboratory.

DMSO has been investigated in the past for various biochemical uses, for example as a reaction solvent for preparing derivatives of various proteins and antibiotics, as an extraction solvent for various proteins, as an analytical solvent and as a solvent for various other laboratory uses. It has also been suggested as a solvent for certain pesticides (see, for example, U.S. Pat. No. 3,068,142).

DMSO has been investigated as a preservative agent for in vitro storage of chilled or frozen tissue and it has also been determined to have a protective effect in experimental animals subjected to X-irradiation following injection of DMSO into such animals.

In connection with topical application of the antifungal griseofulvin, DMSO has been listed along with various inert materials as "bland, high boiling fluids" to be used as carriers for the griseofulvin in applying it to the skin to control fungus growth in the skin (see British Pat. No. 810,377). DMSO has been employed as a solvent for preparation of certain injectable formulations, namely chloramphenicol and an anthelminic preparation (see U.S. Pat. Nos. 3,044,936 and 3,067,096).

Despite the employment of DMSO as a solvent for these purposes and despite general experimentation with DMSO in the medical field, the unique ability of DMSO to alter membrane permeability and to thereby enhance penetration of physiologically active agents was neither suggested nor discovered. Although DMSO has been a well known and widely investigated solvent for many years, its unique ability to enhance penetration of external and internal membrane barriers as contemplated in the present invention has been totally unrecognized.

My co-pending application Ser. No. 753,231 is directed to utilizing DMSO to enhance penetration of various categories of physiologically active agents, including antineoplastic agents, antigens, antihistaminic agents, neuropharmacologic agents, diagnostic dyes and radiopaque agents and nutrients. Many of these categories are unrelated to steroids but some, such as antineoplastic agents and antiinflammatory agents, comprehend the various steroids having the indicated physiological activity. The present application is directed specifically to physiologically active steroids inclusive of those steroids having activities falling within the categories of my co-pending application and those that do not.

SUMMARY OF THE INVENTION

By a mechanism or mechanisms not yet fully understood, DMSO, when applied to animal tissue, increases the permeability of the tissue in a reversible manner to cause a much greater penetration rate for conjointly applied physiologically active agents, and specifically steroids. Although the mode of activity is still unclear, it is definitely not that of the simple "vehicle" or "carrier" since the effect may be obtained to some extent even when the DMSO is applied to tissue separately and the enhanced penetrability of the tissue may last for as much as three hours after the DMSO treatment.

When applied to the intact skin along with dimethyl sulfoxide, particularly at a DMSO concentration of 50% by weight and above, or to skin pretreated with the dimethyl sulfoxide, a steroid may penetrate rapidly to and saturate the stratum corneum (the highly resistant "horny layer" of the skin which is the major barrier to penetration). The steroid continues to penetrate through the skin from this "reservoir" in the stratum corneum to the underlying tissue and into the circulatory system.

Similarly, penetration into underlying tissues and into the circulatory system may be obtained from topical application to the mucous membranes of the body cavities as in the case of intraoral, conjuctival sac, rectal, vaginal and bladder instillation administration, particularly where the DMSO is utilized at a concentration of 10% by weight and above. It is thus seen that a particularly important aspect of this invention is that penetration of agents, and specifically steroids, may be effectively enhanced following topical administration. As used in this connection herein, the term "topical" is intended to include application to all external membrane barriers, including the cutaneous or epidermis regions and the mucous membranes, including the gastrointetinal tract, the respiratory tract and the genitourinary tract.

Important advantages are also obtained through the injection routes for physiologically active steroidal agents. When these agents are injected into the tissues either in a composition including dimethyl sulfoxide (preferably at DMSO concentrations exceeding 1% and especially in the range of 10-20% by weight) or together with conjoint but separate application of DMSO to the tissues, the effect is an enhanced and more even distribution thereof into the tissues surrounding the injection site compared with conventional injection techniques. This more even distribution is of considerable advantage for both local and system effect for all of the usual injectable routes, e.g. subcutaneous, intramuscular, intraperitoneal, etc.

Where a local effect is desired, the intimate distribution of the steroidal agent in the tissue near the site of injection prolongs and enhances its physiologic activity at this local site. This may permit use of a lower dose to achieve the desired response with a smaller risk of side effects which may result from a higher dose.

For all routes of administration, conjoint application of DMSO along with physiologically active steroidal agents having an activity site in the individual cells of the host may additionally result in an enhanced effect of the agent through the ability of DMSO to increase the permeability of such individual cells to such agents.

As previously indicated, the mechanisms of penetration enhancement are as yet not fully elucidated. Accordingly, it is not believed that DMSO acts by several mechanisms in enhancing penetration. DMSO is believed to act directly on tissue to alter the general permeability of the tissue membrane. More specifically, DMSO when applied thereto is believed to decrease the natural resistance of tissue membranes to penetration by foreign agents. DMSO is also believed to promote penetration by a direct transport effect, perhaps by the mechanism of complexing with the agent. This mechanism is beliebed more applicable to cationic and anionic agents.

GENERAL DESCRIPTION OF THE INVENTION

This invention is applicable to the tissue or organisms of all animal phyla, DMSO having differing degrees of influence on penetration of various tissue types of a given animal. Animals of particular importance in the practice of the invention are the mammalians, especially man and veterinary animals. However, the invention may also be practiced with other vertebrates, as for example the amphibians, fishes, reptiles, etc., and with the lower species comprising the non-vertebrates.

As indicated previously, a measure of penetration enhancement may be obtained where the tissue is pretreated with DMSO prior to application thereto of the physiologically active steroidal agent. The tissue penetrability is thus altered by such pretreatment and this reversible effect gradually diminishes and the tissue returns to its normal permeability state. However, for convenience and optimal effect, it is frequently desirable to administer the DMSO and the agent simultaneously in the same composition.

Penetration enhancement is generally non-selective in terms of the type or physiological effect or effects of agents to be transported across membrane barriers. The extent of penetration enhancement will depend upon many factors, the predominant factors being the relative natural permeability of the particular membrane, the concentration of DMSO applied, the extent of solubility of the agent in DMSO and the chemical and physical properties of the agent.

The size of the compound obviously may influence to some extent the relative ability of steroidal agents to penetrate tissue. However, effective membrane penetration utilizing DMSO has been demonstrated for extremely large compounds, for example compounds having molecular weights exceeding 40,000. Even for such a formidable membrane barrier as intact human skin, quite large compounds have been demonstrated to be effectively enhanced.

Standard occlusion techniques frequently may increase the percutaneous absorption of the larger molecules. In general, at least a limited degree of solubility of the agent in DMSO is desirable to achieve maximum benefit of the present invention. Naturally, the practitioner will select steroidal agents, routes of administration and composition forms guided by these well known principles.

Steroids are generally classed as organic molecules which have in common a perhydrocyclopentanophenanthrene nucleus and they are so named because they are related to and usually derived from sterols found abundantly in nature in animal and plant fats. Certain steroids are naturally produced in the body and they act as hormones to mediate and control many body functions. These hormones have been isolated or produced synthetically and used in replacement therapy for hormone deficiencies. Additionally and importantly, these steroids have been found to be highly useful drugs in the treatment of a wide range of disease states not primarily due to lack of hormones. In the recent past, extensive research effort has resulted in the synthesis of a vast number of new steroid hormone derivatives having biological activity (in excess of 1,500 compounds) and the list is growing rapidly. Such derivatives usually contain modifying groups linked to the steroid as by modifying, prolonging or increasing its activity, increasing stability and/or modifying its solubility characteristics. These modifying groups usually comprise addition salts to influence solubility of a side chain substitution on one or more reactive ring carbon atoms. The side chain may be a direct substitution for a ring hydrogen, an ester formed at a reactive hydroxyl group or an ether group. Many of these steroid derivatives have a higher potency than the naturally occurring steroid hormones, often with a decrease in the undesirable side effects which frequently result from administration of the natural steroids. As used herein, the term "steroids" and "steroidal agents" is intended to comprehend both the natural steroids and the biologically active modifications, derivatives and equivalents.

Steroid drugs may have one or more of many types of biological activity such as anabolic, androgenic, glucocorticoid, mineralocorticoid, estrogenic, progestogenic, lipoidiatic (removal of stored fat), circulatory system activity, central nervous system activity, anti-cancer and anti-osteoporic. Some steroid drugs have the ability to block the activity of other hormones, including the activity of other steroids. Their biological activity may be characterized as antiandrogenic, antiglucocorticoid, antimineralocorticoid (diuretic), antiestrogenic and antiprogestogenic. The term "physiologically active" in describing steroidal agents herein is intended to comprehend all of these and any other useful activities. Various activities will be considered hereinafter in connection with specific embodiments of this invention.

The concentration of the DMSO applied to enhance penetration may vary over wide limits. The concentration selected is desirably related to the route of administration to be employed. For cutaneous application, compositions including at least about 50% by weight DMSO are preferable in that they have been found to increase percutaneous penetration in a highly significant manner. Maximum cutaneous penetration is generally attained with DMSO concentrations closely approaching 100% (excluding the agent), but with concentrations much above 90% by weight the incremental increase in penetration rate over that achieved at 90% often is relatively small. On the other hand, above a 90% concentration of dimethyl sulfoxide, the side effects of a burning sensation and erythema increase significantly. Accordingly, for topical use, it may be desirable, consistent with physical stability of the composition, to formulate the DMSO in compositions containing a DMSO concentration of between about 50% and 90% by weight and containing water, preferably 10% by weight or greater.

Application to mucous membranes follows generally the procedure for cutaneous administration. However, lower concentrations of DMSO, for example as low as 10% by weight, may be preferred since penetration of mucous membrane is more easily affected.

For most injection routes, preferably lower concentrations of DMSO of about 10% to about 20% by weight are utilized. For some injection routes, for example intra- and peri-articular routes, higher concentrations, say 30-40%, may be preferred.

The amount of the physiologically active steroidal agent to be administered will obviously be an effective amount for the desired result expected therefrom. This, of course, will be ascertained by the ordinary skill of the practitioner. Due to enhanced activity which may be achieved through better penetration, the dosage of agent may often be decreased from that generally applicable. In accordance with the usual prudent formulating practices, a dosage near the lower end of the useful range of the particular agent may be employed initially and the dosage increased as indicated from the observed response, as in the routine procedure of the physician.

As previously discussed, the DMSO may advantageously be compounded with the physiologically active steroidal agent for concurrent administration. The usual pharmaceutical compounding agents, diluents or carriers may be included in these compositions as desirable for the particular route of administration and dosage form. The amount and type of diluent or carrier used should, of course, be consistent with the compatability of the agent in DMSO and the diluent. A co-solvent, or other standard adjuvant such as a surfactant may be called for to maintain the agent in solution or suspension at the desired concentration. Where stability of the agent in the presence of DMSO at the desired concentration is a problem, it may be desirable to prepare the formulation immediately before administration or to administer the DMSO and the agent separately to the tissue.

In selecting the route of administration for a given agent, obviously the known toxicity, side effects and effectiveness for a given route of administration should be taken into account. For example, due to skin irritation known to be caused by some agents or due to poor penetration characteristics, some other route than dermal application may be the route of choice for such agents.

Dosage forms for topical application may include solutions (paints), nasal sprays, lotions, ointments (including creams and gels), suppositories and the like. The solutions and nasal sprays may simply comprise the agent dissolved in DMSO, optionally with an amount of water, glycerine or other diluent. For nasal sprays and other mucous membrane applications, isotonic saline may be preferable as a diluent. The DMSO may be present in these forms in various concentrations, say from about 10% to about 75% by weight or higher.

Lotions and gels, ointments or creams may contain the usual ingredients to provide a base, as for example cetyl alcohol, an emulsifier such as lauryl sulfate, and water. Another base may be formulated by combining equal weight amounts of stearic acid, cetyl alcohol, triethanolamine and glycerol monostearate with water. Still other bases may utilize polyethylene glycols of different viscosities, depending upon the desired consistency. DMSO may be added to the lotion or ointment base in varying amounts as desired, generally up to around 50% by weight.

A suppository form may be made from a high viscosity polyethylene glycol 4,000, water and DMSO, which may be present in an amount of about 20% by weight.

The concentration of physiologically active steroidal agent in the various dosage forms is, of course, commensurate with that normally utilized for the particular agent in conventional formulations for effective results for the intended route. Both the amount of physiologically active steroidal agent and the amount of DMSO will be influenced by the type of effect desired. If a more localized effect is required, as for example in treating a skin condition, lower amounts of physiologically active steroidal agent and lower concentrations of DMSO may be called for. Where deeper penetration is desired, a higher concentration of DMSO may be desirable to promote adequate penetration. Where general systemic concentration of an agent is desired for a topical preparation, generally higher concentrations of DMSO are desirable and the amount of steroidal agent may be included in the composition sufficient to provide the blood level desired.

The various pharmaceutical forms are desirably provided in determined amounts, as in containers of a given volume. These amounts may include 100% DMSO concentration containing the desired dose of the agent, or a lesser concentration of DMSO with a diluent and the physiologically active agent dose. Thus, for example, graduated ampules containing, say, 5 cc. of 100% DMSO with the agent dissolved therein may be provided. The practitioner need only open and dispense all or a determined part to a subject. Nasal spray bottles, aspirators, suppositories, cotton tipped stick applicators, squeeze tubes may all be utilized for topical application.

The following illustrates the practice of the present invention with various classes of steroidal agents.

DESCRIPTION OF PREFERRED EMBODIMENTS

Glucocorticoids

Hormones produced naturally in the body by the adrenal cortex are called adrenal cortical steroids or corticoids. Some corticoids, predominantly cortisone and hydrocortisone, have the property of influencing the rate of metabolism of glucose. Hence they, along with their derivatives and modifications, are called glucocorticoids. Glucocorticoids have other predominant physiologic activity which makes them highly useful as drugs. One of the most important activities is the suppression of inflammation, particularly in the treatment of arthritis and rheumatic diseases. Glucocorticoids are also useful in the treatment of dermatoses, drug reactions, bronchial asthma, lupus erythematosus, angioneuroedema and many other disorders. Massive doses of corticosteroids have also been used to induce remissions in leukemia. Glucocorticoids are generally, 3-keto, $\Delta$ 4,11-oxygen function (hydroxy or keto), 20-keto steroids of the pregnane series. Typically they also have a 21-hydrogen, halogen or hydroxy function. The 11-hydroxy glucocorticoids are of particular interest for local application with DMSO due to their ability to induce local effects. DMSO may be combined with glucocorticoids to enhance their penetration to the affected tissue for these various disorders. The following examples illustrate compositions and treatments for this purpose utilizing the most prominent and active natural and modified glucocorticoids.

EXAMPLE 1

Penetration of Injected Corticosteroids

A thirty-two year old white woman was seen with a two days' history of left subdeltoid bursitis. This gave her pain on minimal abduction particularly, but also was present in other movements of the shoulder joints. Physical examination revealed marked tenderness to pressure with obvious protective muscle spasm overlying the joint. Two ml of hydrocortisone was injected into the bursal area. This was associated with three hours' relief of pain. The patient was seen again two days later. At this examination her pain was just as marked as the first visit. Two ml. of hydrocortisone was injected and 5 cc. of 100% dimethyl sulfoxide was applied liberally to the entire left shoulder area. Within 15 minutes all pain disappeared and the patient reported no return of her symptoms when examined one week later.

EXAMPLE 2

Penetration of Injected Corticosteroids

A forty-two year old white male was examined with a one week history of acute subdeltoid bursitis of the right shoulder. Four mg. of Decadron was injected into the right subdeltoid bursa. The patient estimated that about a 20% relief of his discomfort was attained. Full pain returned one day later. At this point he was reinjected with 4 mg. of Decadron and 4 cc. of 100% dimethyl sulfoxide was placed on the skin over the involved bursa. This time the pain disappeared completely and did not recur.

Both of the above examples show that cortisone injected for subdeltoid bursitis is obviously of benefit, but that its relief of symptomatology is enhanced with the simultaneous application of dimethyl sulfoxide to the skin.

EXAMPLE 3

Penetration of Corticosteroids

A twenty-four year old medical student was seen with atopic dermatitis of the right antecubital fossa. Three cc. of 100% dimethyl sulfoxide was applied four times daily for three days. No benefit was noted. One mg. or ¼ cc. of Decadron (dexamethansone 21-phosphate) was applied four times a day for two days without benefit. One mg. of dexamethasone 21-phosphate in 3 cc. of 100% dimethyl sulfoxide was painted onto the involved area four times daily for three days. At the end of this period all evidence of the inflammatory reaction had disappeared.

This example shows an improved action of dexamethasone 21-phosphate when used with dimethyl sulfoxide.

EXAMPLE 4

The following lotion formulation may be prepared containing about 0.01 to 1.0%, and preferably 0.1% fluocinolone acetonide:

| Fluocinolone acetonide | 0.1-1.0 gm |
|---|---|
| Cetyl alcohol | 200 gm |
| propylene glycol | 100 gm |
| Sodium lauryl sulfate | 15 gm |
| DMSO | 300 gm |
| Water | qs 1000 cc |

The steroid is dissolved in the DMSO and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of the steroid into the inflamed tissue in enhanced and a therapeutic level is achieved more rapidly than when the steroid is applied in conventional formulations.

EXAMPLE 5

The following ointment (gel) formulation may be prepared containing about 0.2% to 1.0%, and preferably 0.6% triamcinalone acetonide:

| Triamcinalone acetonide | 0.2-10 gm |
|---|---|
| Polyethylene glycol 400 | 400 gm |
| Dimethyl sulfoxide | 598 gm |
| Carboxy vinyl polymer powder | 1 gm |
| Triethylanolamine | 0.4 gm |

The corticosteroid is dissolved in a mixture of the first two ingredients and the carboxy vinyl polymer gelling agent is sprinkled on the surface of the combined liquids and stirred until all the particles have been wetted and dispersed. The triethanolamine is then added dropwise to the mixture until it has gelled, care being taken to minimize the air entrapment. This gel is particularly effective in the treatment of seborrhea and other scalp and hair inflammatory conditions and may be applied in amount of frequency conventionally used for topical application of this steroid. Better penetration and thereby an increased antiinflammatory active is obtained for the amount of steroid applied than results from its application in conventional formulations.

EXAMPLE 6

The following ointment formulation may be prepared containing about 0.1% to 1.0% prednisone and preferably 0.5%:

| Prednisone | 0.1-10 gm |
|---|---|
| Glyceryl monostearate, acid type | 180 gm |
| Stearyl alcohol | 50 gm |
| Polysorbate 80 | 20 cc |
| Water | 450 cc |
| Dimethyl sulfoxide | 300 cc |

The product is prepared as described in Example 4. The ointment is a valuable base for application of the corticosteroid to inflammatory dermatological areas, particularly when they require inunction. Application is in accordance with that usual for topical application of this steroid in conventional bases.

EXAMPLE 7

The following cream formulations may be prepared containing about 0.1% to 1% 16a-methyl prednisolone and preferably 0.5%:

| 16a-methyl prednisolone | 0.1-10 gm |
|---|---|
| Stearic acid | 200 gm |
| Glyceryl monostearate, acid type | 200 gm |
| Sodium lauryl sulfate | 20 gm |
| Dimethyl sulfoxide | 200 gm |
| Water | qs 1000 cc |

As above, the product is prepared as directed in Example 4 and is useful in severe dermatoses requiring inunction.

MINERALOCORTICOIDS

Some natural corticoids have the predominant property of inducing sodium retention (depressing the rate of excretion of sodium salts through the kidneys). Hence, they, along with their derivatives and modifications, are called mineralocorticoids. The principal natural mineralocorticoid is aldosterone, while desoxycorticosterone is the most prominent synthetic mineralocorticoid. Both are useful in treating the mineralocorticoid deficient state in Addison's disease. The following exemplifies the use of DMSO in the administration of mineralocorticoids to enhance penetration:

EXAMPLE 8

The following ointment formulation may be prepared containing about 0.5% to 2.5%, preferably 1.0%, desoxycorticosterone acetate:

| Desoxycorticosterone acetate | 5-25 gm |
|---|---|
| Stearic acid | 300 gm |
| Cetyl alcohol | 100 gm |
| Polysorbate 20 | 20 cc |
| Sorbital 70% | 100 cc |
| Dimethyl sulfoxide | 300 cc |
| Water | qs 1000 cc |

The product is prepared as specified in Example 4. The product may be employed in treatment of pigmentation in Addison's disease by topical application to the affected area. Penetration may be increased sufficiently so that effective results may be obtained. In conventional bases this steroid has had very limited effectiveness topically and injection usually must be resorted to.

ANDROGENS

Androgen is the generic term which comprehends testosterone, the natural male hormone, androsterone and the modifications and derivatives thereof which have masculinizing activity. Natural and modified androgens are employed in replacement therapy for hypogonadal males. Typical for this purpose are the isobutyrate, decanoate, isocaproate, enanthate, phenylproprionate and cyclopentylproprionate esters of testosterone and 17-methyl testosterone.

However, a much more important drug roll for these steroids is their use as antiestrogens in treatment of female genital cancer and as anabolic agents (metabolism stimulation) in treating debilitated subjects. For these purposes, androgens which have been modified to decrease their unwanted virilizing effects (while retaining their anabolic and antiestrogenic activity) are generally preferred. The following steroids exemplify these compounds with the commercial source of the compounds indicated:

17a-ethyl-19-nortestosterone (Nilevar)
17a-methyl-19-nortestosterone (Syntex Product)
19-nortestosterone phenylproprionate (Durabolin)
9a-fluoro-11B-hydroxy-17a-methyltestosterone (Halotestin)
4-chloro-19-nortestosterone acetate
4-hydroxy-17a-methyl testosterone (Oranabol)
2-hydroxymethylene-17a-methyl-dihydrotestosterone (Adroyd-Parke Davis)
17a-methyl-17-B-hydroxyandrostano (3,2,-C)-pyrazole (Androstanazole)
1-dehydro-17a-methyltestosterone (Dianabol)

The following examples illustrate the use of DMSO to enhance the penetration of androgens:

EXAMPLE 9

A suppository formulation may be prepared as follows containing about 1 to 5%, preferably 2%, testosterone propionate:

| Testosterone propionate | 10–50 gm |
|---|---|
| Polyethylene glycol 4000 | 400 gm |
| Propylene glycol monostearate | 100 gm |
| Dimethyl sulfoxide | 500 cc |

The solid constituents are melted, added to the solution of the steroid in DMSO and poured into an appropriate mold. The product is recommended for rectal application as replacement therapy.

EXAMPLE 10

A suppository formulation may be prepared as follows containing about 1% to 5%, preferably 2%, 17-methyl testosterone:

| 17-methyl testosterone | 1–50 gm |
|---|---|
| Hydrogenated castor oil | 400 gm |
| Stearic acid | 100 gm |
| Dimethyl sulfoxide | 500 cc |

The product is prepared as noted in Example 9 and used in a similar manner.

EXAMPLE 11

A cream formulation may be prepared as follows containing about 1% to 10%, preferably 3%, 17a-ethyl-19-nortestosterone:

| 17a-ethyl-19-nortestosterone | 10–100 gm |
|---|---|
| Cetyl alcohol | 250 gm |
| Stearyl alcohol | 200 gm |
| Polysorbate 80 | 20 cc |
| Water | 250 cc |
| Dimethyl sulfoxide | qs 1000 cc |

This cream may be prepared as noted in Example 4. It may be applied topically for stimulation of epithelization and connective tissue regeneration.

EXAMPLE 12

A lotion or paint formulation may be prepared as follows containing about 1% to 5%, preferably 2%, testosterone propionate:

| Testosterone propionate | 10–50 gm |
|---|---|
| Dimethyl sulfoxide | 890 gm |
| Water | 100 gm |

The steroid is dissolved in a mixture of the dimethyl sulfoxide and water. The formulation may be applied topically as an anabolic and in the treatment of breast cancer. The enhancement of penetration over that obtained with conventional topical formulations permits more effective topical use of this steroid which previously had to be injected to achieve a response in many cases.

EXAMPLE 13

The following cream may be formulated with the following composition containing about 1% to 10%, and preferably 3%, 2a-methyl-dihydrotestosterone propionate (metholone):

| Metholone | 10–100 gm |
|---|---|
| Stearyl acid | 200 gm |
| Glycerol monostearate, acid type | 200 gm |
| Sodium lauryl sulfate | 20 cc |
| Water | 400 cc |
| Dimethyl sulfoxide | 200 cc |

The cream is prepared as directed in Example 4. The product is useful in the treatment of muscle wasting and weakness following breast cancer surgery and may be applied topically to the affected area. Penetration of the steroid is greatly improved over that obtained in conventional formulations.

EXAMPLE 14

The following ointment (gel) may be formulated containing about 1% to 5%, preferably 2%, steroid:

| 2-hydroxymethylene-17a-methyl-dihydrotestosterone | 10–50 gm |
|---|---|
| Propylene glycol | 500 cc |
| Dimethyl sulfoxide | 498 cc |
| Carboxy vinyl polymer powder | 1 gm |
| Triethanolamine | 0.5 gm |

The product is prepared as specified in Example 5. The product is useful in topical anabolic treatment, particularly in preventing thinning of the skin and in inducing blood vessel thickening.

ESTROGENS AND PROGESTINS

Estrogen is the generic name for estradiol and its active metabolites estrone and estriol, naturally occurring female sex hormones, and their derivatives and modifications. Estrogens are useful in treating menstruation disorders, infertility, habitual abortions and endometriosis. Along with progestrogens, they are used to control the reproductive cycle in women for contraception. They are also used in replacement therapy, particularly in treating the hormone deficiency states such as in postmenopausal women. Modified estrogens having lower feminizing characteristics are particularly useful for other applications, including the treatment of antherosclerosis and osteoporosis. Their antiandrogenic effects are also useful in the treatment of prostatic cancer.

Progesterone is a natural female hormone which plays a primary role in the reproductive cycle of the female mammal, particularly in the menstrual cycle of the primate. Progesterone and its modifications and derivatives are classified as progestins. Progestins are useful in replacement therapy and in treatment of menstrual disorders and prevention of fetal loss. A number of modified progestogens are useful in contraception. The various modified progestogens include the 19-nor-progestogens, the 17a-methyl progestogen derivatives, the 3-enol esters of progesterone and 17-acetoxyprogesterone and the 9-iso-10-iso compounds called retroprogesterones.

The following exemplifies the practice of this invention with estrogenic and progestenic steroids:

EXAMPLE 15

The following lotion may be formulated as follows containing about 0.1% to 1.0%, preferably 0.4%, estradiol valerate:

| Estradiol valerate | 1-10 gm |
| --- | --- |
| Cetyl alcohol | 200 gm |
| Propylene glycol | 100 gm |
| Sodium lauryl sulfate | 15 gm |
| Water | 400 cc |
| Dimethyl sulfoxide | 300 cc |

This product is prepared as noted in Example 4. The product is designed as a means of establishing systemic replacement therapy for estrogens during menopause by simple topical application to the skin or mucous membrane. The DMSO enhances penetration of the estrogen sufficiently to obtain a systemic effect. This has not been possible in conventional formulations.

EXAMPLE 16

A suppository may be formulated as follows to contain 0.1 to 1.0%, preferably 0.5%, of 3-methyl ether of etheynylestradiol:

| 3-methyl ether of ethylnylestradiol | 10-100 gm |
| --- | --- |
| Polyethylene glycol 4000 | 400 gm |
| Propylene glycol monostearate | 100 gm |
| Dimethyl sulfoxide (DMSO) | 500 cc |

The suppositories are prepared as noted in Example 9. The product is used in estrogenic replacement therapy and may be used by rectal or vaginal application.

EXAMPLE 17

The following ointment (gel) may be formulated containing 0.1% diethylstilbesterol:

| Diethylstilbesterol | 1 gm |
| --- | --- |
| Propylene glycol | 500 cc |
| Dimethyl sulfoxide | 498 cc |
| Carboxy vinyl polymer powder | 1 gm |
| Triethanolamine | 0.5 gm |

This gel is prepared as detailed in Example 5. The preparation is particularly suitable for topical application in the treatment of adolescent acne.

EXAMPLE 18

A cream may be formulated as follows to contain about 0.72% norethynodrel and about 0.0286% mestranol:

| Norethynodrel | 10.5 gm |
| --- | --- |
| Mestranol | 0.42 gm |
| Cetyl alcohol | 100 gm |
| Stearyl alcohol | 100 gm |
| Polysorbate 80 | 20 cc |
| Water | 250 cc |
| Dimethyl sulfoxide | qs 1000 cc |

This cream is prepared as noted in Example 4. This formulation is to be used as a contraceptive agent applied cutaneously twice monthly at a dosage of 10 grams.

EXAMPLE 19

A suppository formulation may be prepared as follows:

| Chlormadinone | 5 mg |
| --- | --- |
| Stilbesterol | 1 mg |
| Polyethylene glycol 4000 | 400 gm |
| Propylene glycol monostearate | 100 gm |
| Dimethyl sulfoxide | 500 cc |

The suppositories are formed as in Example 9. The product may be employed for treatment of irregular or prolonged bleeding.

EXAMPLE 20

A suppository formulation may be prepared by melting together the following:

| Estradiol valerate | 2.75 gm |
| --- | --- |
| Guiacol glycerol stearate | 100 gm |
| Dimethyl sulfoxide | 300 gm |
| Diglycol laurate | 150 gm |

The melted blend is poured into a suppository mold to provide 10 gm. suppositories for treatment of prostatic cancer.

SPIROLACTONES

Hypersecretion of aldosterone (primary aldosteronism) as a primary event or secondary to other disease states, such as cardiac, renal and hepatic disorders (secondary aldosteronism) may cause undesirable salt and water retention and promote edema. A certain steroid series, the 17-spirolactosteroids or spirolactones, possesses an antialdosterone activity capable of blocking the effects of aldosterone on the kidney. Hence, they are called aldosterone antagonists. The following example describes use of the spirolactones:

EXAMPLE 21

The following ophthalmic formulation may be prepared containing about 0.1% to 0.75%, preferably 0.3%, spironolactone:

| | |
|---|---|
| Spironolactone | 1–7.5 gm |
| Polyethylene glycol 4000 | 200 cc |
| Dimethyl sulfoxide | 200 cc |
| Water | qs 1000 cc |

The formulation is prepared by melting the polyethylene glycol 4000, dissolving the steroid in the DMSO, mixing the two liquids together and diluting to volume with water while stirring. The preparation is applied topically to the eye by eye dropper, or similar applicator, for treatment of glaucoma.

What I claim is:

1. A method of enhancing the penetration into and across an external membrane barrier of a human or animal subject to a physiologically active steroidal agent capable of eliciting a physiological effect upon topical application thereof, which comprises the concurrent topical administration to the external membrance of an amount of said steroidal agent effective to produce the desired physiological effect and an amount of DMSO sufficient to effectively enhance penetration of said steroidal agent to achieve the desired physiological effect.

2. A method as in claim 1 and where in the said agent is applied to the intact skin in a composition which includes said DMSO and wherein the DMSO in said composition is at least about 50% by weight of the composition.

3. A method as in claim 1 and wherein said agent is applied to mucous membrane of a body cavity in a composition which includes said DMSO and wherein the DMSO in said composition is at least about 10% by weight of the composition.

4. A method as in claim 1 and wherein said agent is a non-estrogenic steroid.

5. A method as in claim 1 and wherein said steroidal agent is a steroid of the pregnane series.

6. A method as in claim 1 and wherein said agent is applied to said membrane in a composition which includes said DMSO.

7. A method as in claim 6 and wherein said composition contains a pharmaceutically acceptable thickening agent in an amount sufficient to materially increase the viscosity thereof, whereby to facilitate topical application.

8. A method as in claim 7 wherein said composition is in the form of an ointment.

9. A method as in claim 7 and wherein said composition is in the form of a lotion.

10. A method as in claim 7 and wherein said composition is in the form of a suppository.

* * * * *